United States Patent [19]

Lester

[11] Patent Number: 4,669,310
[45] Date of Patent: Jun. 2, 1987

[54] HIGH FREQUENCY ULTRASONIC TECHNIQUE FOR MEASURING OXIDE SCALE ON THE INNER SURFACE OF BOILER TUBES

[75] Inventor: Samuel R. Lester, Lynchburg, Va.

[73] Assignee: The Babcock & Wilcox Company, New Orleans, La.

[21] Appl. No.: 844,399

[22] Filed: Mar. 26, 1986

[51] Int. Cl.⁴ ..................... G01N 29/00; G01B 17/02
[52] U.S. Cl. ......................................... 73/597; 73/629; 73/1 J
[58] Field of Search ............... 73/597, 629, 1 J, 10 V, 73/1 R, 86; 422/53

[56] References Cited

U.S. PATENT DOCUMENTS

| | | | |
|---|---|---|---|
| 3,056,284 | 10/1962 | Marsh et al. | 73/597 |
| 3,165,923 | 1/1965 | Lund | 73/629 |
| 3,228,232 | 1/1966 | Proctor | 73/597 |
| 3,587,299 | 6/1971 | Foley | 73/629 |
| 4,289,031 | 9/1981 | Tominaga et al. | 73/597 |
| 4,446,736 | 5/1984 | Jackson | 73/629 X |
| 4,545,248 | 10/1985 | Kitada et al. | 73/597 |

FOREIGN PATENT DOCUMENTS

| | | | |
|---|---|---|---|
| 2817247 | 11/1978 | Fed. Rep. of Germany | 73/597 |
| 150810 | 9/1983 | Japan | 73/629 |
| 611015 | 6/1978 | U.S.S.R. | 73/597 |

OTHER PUBLICATIONS

"Measurement of Applied and Residual Stresses Using an Ultrasonic Instrumentation System"; *ISA Transactions*, vol. 19, No. 2, pp. 33–40; 1980; B. E. Gordon, Jr.
"Ultrasonic Detection of Calcium Sulfate Scale on Metal Surfaces"; U.S. Dept. of Interior, Office of Saline Water, Research and Development Progress Report No. 444; Fred R. Rollins, Jr., et al.; Jun. 1969; 39 pages.

*Primary Examiner*—Michael J. Tokar
*Assistant Examiner*—Tom Noland
*Attorney, Agent, or Firm*—Vytas R. Matas; Robert J. Edwards

[57] ABSTRACT

A method is disclosed for ultrasonically detecting and measuring oxide scale on the inner cylindrical surface of a fluid containing boiler tube, in situ, within a boiler. An ultrasonic pulse is directed into the tube. The time of flight of the ultrasonic pulse within the scale is determined. The determined time is correlated to the thickness of the scale.

4 Claims, 3 Drawing Figures

HIGH FREQUENCY ULTRASONIC TECHNIQUE FOR MEASURING OXIDE SCALE ON THE INNER SURFACE OF BOILER TUBES

BACKGROUND OF THE INVENTION

This invention relates to nondestructive examination of boiler tubes and, in particular, to the ultrasonic detection and measurement of the thickness of oxide scale on the inner cylindrical surface of boiler tubes.

Scale deposits on the waterside of boiler tubes undesirably increase heat transfer resistance and have long been recognized as a cause of boiler tube failure. In the electric utility industry, a metallurgical technique is typically employed to measure scale thickness to predict the remaining life of high pressure boiler tubes.

With the metallurgical measuring technique, a sample of the boiler tube is removed from the boiler and a new section of tubing is installed in its place. The sample is sent to a metallurgical laboratory. A nickel coating is applied to the sample to prevent the scale from breaking loose during sample preparation. Next, small sections are cut from the tube sample, mounted, polished, etched and examined under a metallurgical microscope. Once measured, the thickness of the scale is used in an algorithm to predict the remaining life of the boiler tube.

Metallurgical examination provides a very accurate measure of scale thickness. However, such examinations inconveniently require physical removal and replacement of boiler tube sections and analysis of the removed tube sections at laboratory facilities each time a scale thickness measurement is desired. The overall procedure is very time consuming and expensive as it directly relates to downtime, i.e. time loss in ability to generate power.

At the present time, there are no known commercialized nondestructive techniques for measuring or detecting scale on the inner cylindrical surface of boiler tubes. The recovery and utility boiler industries have expressed a need for such techniques.

Ultrasonics are presently utilized, in the inspection of boiler tubes, for example, for detecting surface and subsurface flaws and for the measurement of the thickness of a material or the distance to a flaw. Hence, the development of an in situ, nondestructive boiler tube scale measurement technique, particularly one which employs ultrasonics, would be highly desirable.

SUMMARY OF THE INVENTION

In accordance with the invention, a nondestructive ultrasonic method is provided for measuring scale thickness on the inner cylindrical surface of in-service boiler tubes.

The technique of the invention uses the round trip time difference, referred to as the time of flight (ToF), between the pulse echo reflections at the tube's metal/scale interface and scale/fluid interface as a basis for obtaining a reasonably reliable indication of scale thickness.

More particularly, the invention provides a method for the in situ ultrasonic measurement of oxide scale on the inner cylindrical surface of a fluid containing boiler tube. The method includes the steps of positioning an ultrasonic transducer in an orientation adjacent to the boiler tube and transmitting of an ultrasonic pulse into the boiler tube directed such that the centerline of the ultrasonic beam is perpendicular to the inner tube surface of the boiler tube. The transducer is energized to transmit an ultrasonic pulse having a frequency of at least 50 MHz. The time of flight (round trip time) of an ultrasonic pulse within the scale is determined by measuring the times of flight to the tube/scale and scale/fluid interfaces. A measurement of scale thickness is obtained by correlating the time of flight within the scale to a pre-established standard—either a correlation curve or by formula. The standard, which relates oxide scale thickness to the time of flight of the ultrasonic pulse within the scale, is provided or pre-established by subjecting a plurality of samples of the boiler tube to ultrasonic pulses and then actually measuring scale thickness by physical or metallurgical means. Once the standard is determined by such techniques, further destructive testing of the boiler tubes is no longer necessary.

A feature of the invention is the use of a 50 MHz ultrasonic system for measuring scale as thin as 5 mils.

The inventive technique provides a rapid method for measuring the thickness of scale on the inside surface of boiler tubes without having to continuously remove sections of tubing from the boiler. Because tube samples are not removed, more data points can be obtained in a shorter amount of time. The inventive technique, moreover, permits the examination of many tubes in various locations of the boiler. The availability of additional data enhances the ability to accurately predict the remaining life of the boiler tubing.

BRIEF DESCRIPTION OF THE DRAWINGS

In the accompanying drawings, forming a part of this specification, and in which reference numerals shown in the drawings designate like or corresponding parts throughout the same.

DETAILED DESCRIPTION

Figure 1:
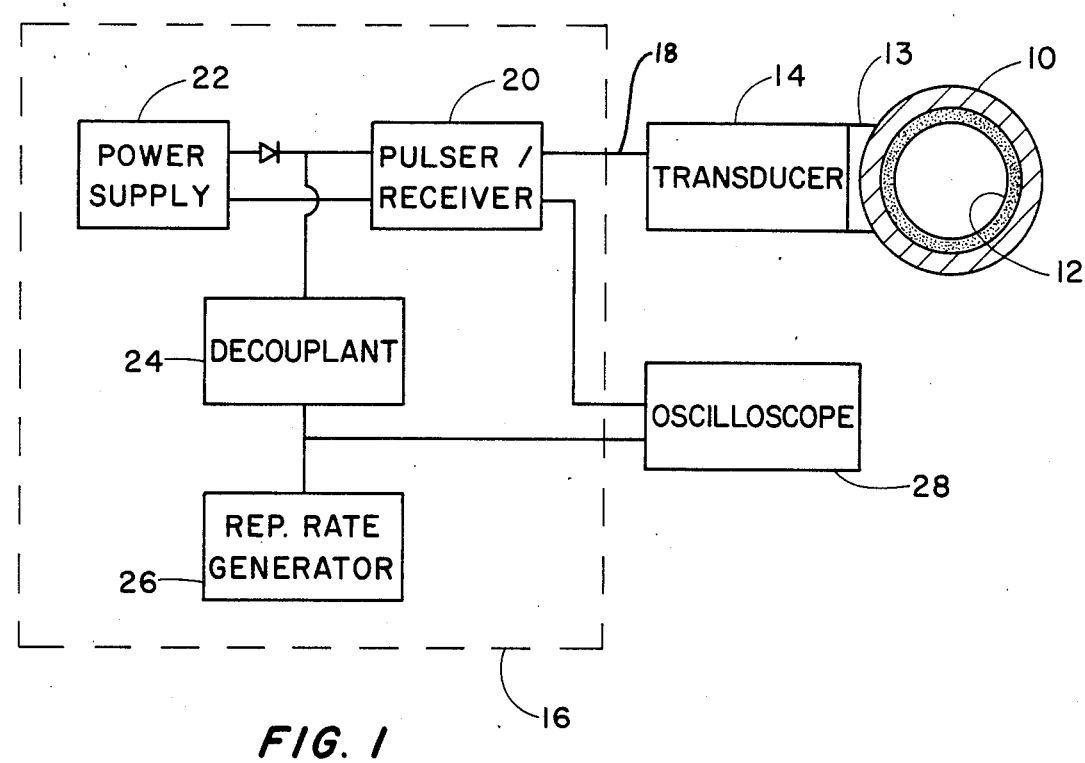
FIG. 1 is a schematic representation of an arrangement for ultrasonically determining the thickness of scale on the inside surface of a boiler tube in accordance with the invention.

FIG. 1 schematically illustrates an arrangement for determining the thickness of scale on the inner cylindrical surface of a boiler tube in accordance with the invention.

In FIG. 1, a cylindrical boiler tube 10 is shown with a layer of scale 12 formed on its inner surface. A handheld contact ultrasonic transducer 14, such as a model V214-BA hand-held transducer produced by Panametrics, Watham, Mass., is positioned on the clean, outer surface of the boiler tube. To facilitate the transmission of ultrasound into and out of the steel tube, a low viscosity couplant 13 is used between the transducer and the steel tube. The illustrated arrangement, enables the ultrasound to penetrate heavy wall boiler tubing and measure the scale. The hand-held technique allows rapid repositioning of the transducer to different locations on a boiler tube or to different boiler tubes.

The transducer 14 is electrically connected via a coaxial cable 18 to a high-frequency pulser/receiver 16 which, in turn, is connected to a delayed time, pulse overlap oscilloscope 28 having a delayed time base and a pulse overlap feature for conveniently and accurately measuring the differential time of flight (ToF).

The transducer 14 is a high frequency transducer. As used herein, high frequency is intended to refer to frequencies of 50 MHz or greater. In a preferred arrangement, the transducer has a circular active element with a diameter of 0.250 inches and operates at 50 MHz. The element is attached to a cylinder of fused silica measuring 0.720 inches in diameter and 0.500 inches thick which produces a delay in the ultrasonic signal of 4.25 microseconds. A Panametric V214-BA transducer has been experimentally used with favorable results.

A model PR 106 pulser/receiver, produced by Metrotek, Richmond, Wash., has been found to be a suitable pulser/receiver. The high-frequency pulser/receiver 16 is a device preferably selected to produce a high frequency pulse of short duration with a wide (60 MHz) band width. This enables an ultrasonic signal to be produced and received that is capable of resolving the energy reflected from both the tube/scale and scale/fluid interfaces. A Panametric 5600 pulser/receiver has also been experimentally used with favorable results. In a preferred arrangement, the high-frequency pulser/receiver 16 consists of a power supply 22, a MetroTek PR 106 pulser/receiver 20, a decoupling device 24 and a rep. rate generator 26. This arrangement operates at 200 volts with a rise time of 6 nanoseconds and a band width of 60 MHz.

The oscilloscope 28 is preferably a high frequency delayed time based oscilloscope. A Tektronik 2236 oscilloscope having a band width of 100 MHz and a delayed time base capable of 5 nanoseconds per division has been used on an experimental basis. This instrument has a pulse overlap capability which can be used for measuring the time of flight in the scale.

The transducer 14 is positioned so that the inside surface of the tube 12 is normal to the ultrasonic beam. An ultrasonic signal is then generated and received by the high-frequency pulser/receiver 16. The signal is displayed on the oscilloscope 28.

Figure 2:
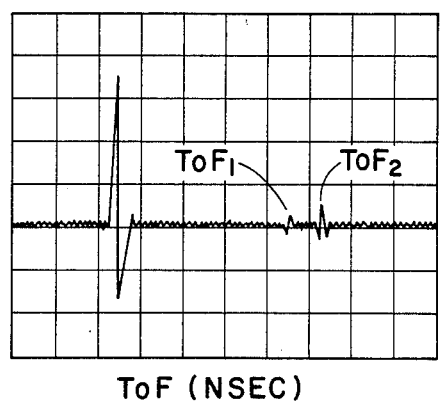
FIG. 2 is an oscillogram of pulse reflections characterizing the response of a boiler tube containing scale.

FIG. 2 is an oscillogram which shows the signals produced on a cathode ray tube display formed by the pulse echo interface reflections of the ultrasonic wave. The impedance mismatch between the tube 10 and the scale 12 formed on the inside surface of the tube 10 causes the ultrasonic wave to be reflected. The amplitude of the reflected signal is related to the impedance ratio between the two materials. The amplitude of the reflected signal increases with greater impedance ratios. Similarly, a reflection occurs at the interface of the scale and fluid within the tube. Since the impedance ratio between the wall and the scale is very small, the signal amplitude is small. However, the impedance ratio between the internal scale and the fluid is larger and, thus, a larger signal is reflected and displayed in the cathode ray tube.

Figure 3:
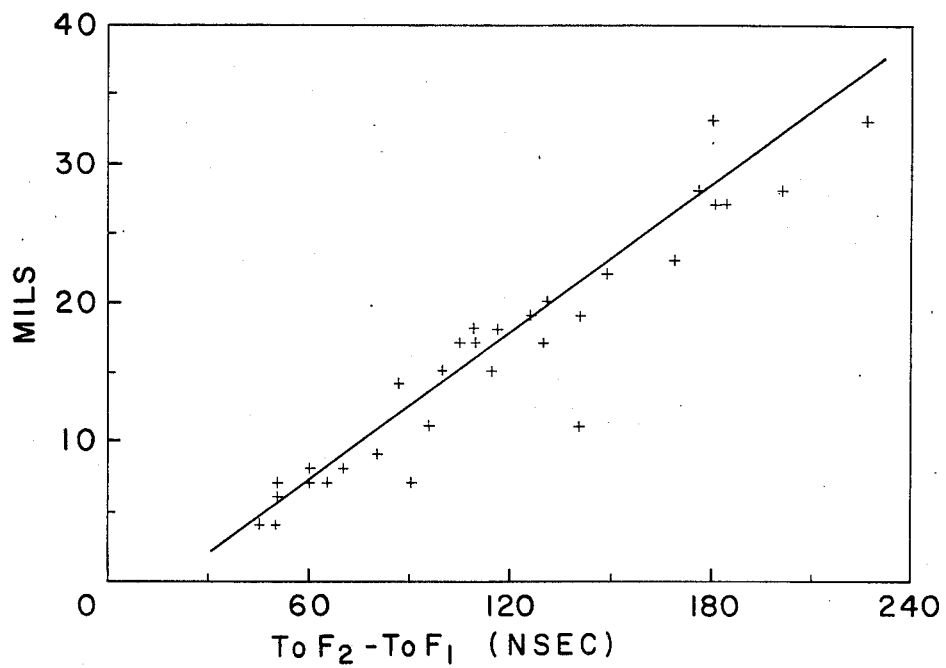
FIG. 3 is a graph depicting a correlation curve illustrating actual thickness of a scale in relation to time of flight of an ultrasonic signal within the scale.

Thus, as shown in FIG. 2, a first time of flight (ToF$_1$) to and from the tube metal/scale interface and a second time of flight (ToF$_2$) to and from the scale/fluid interface are determined. The difference between the first and second times of flight may be correlated via a correlation chart, as shown in FIG. 3, or by formula, in order to determine the thickness of the scale.

The following examples are illustrative and explanatory of portions of the inventive technique.

EXAMPLE

A series of boiler tube samples were cut from a radiant boiler that had run for 219,000 hours or approximately 30 years. The samples were cut from pendant tubes in the reheater section. Samples A through D were made of a ferritic steel with 2.25% chromium and 1.0% molybdenum, marketed under the name Croloy 2¼. The tubes had an outside diameter of approximately 2 inches.

A heavy-oxide coating on the outside of the tubes was mechanically removed.

To measure the scale on the inner surface of the tubes, each sample was mounted on a V-block to stabilize the sample. A 50 MHz, transducer was positioned on the surface of the sample and adjusted so that the inside surface of the tube was normal to the ultrasonic beam. The ultrasonic signal was generated and received using a high frequency pulser receiver. The signal was displayed on a 400 MHz waveform processing oscilloscope, where the time of flight measurements were made.

With the system assembled as described, the time of flight measurements were rapidly obtained.

After completing the ultrasonic measurements, the samples were marked and labeled to indicate locations for metallurgical measurements. The locations were selected so that the data points would be equally distributed over the entire oxide scale thickness range. The scale surface was nickel coated to protect the scale. Then, the samples were mounted, polished and measured.

The results and the metallurgical measurements of the ultrasonic ToF measurements are shown in Table 1.

TABLE 1

| Sample | Location | Ultrasonic Thickness (nsec) | Metallurgical Thickness (mils) |
|---|---|---|---|
| A | 0° | 143 | 22 |
| D | 270° | 167 | 23 |
| A | 90° | 95 | 13 |
| C | 180° | 179 | 33 |
| B | 270° | 226 | 33 |

Statistical analysis of the results in Table 1 indicates that the ultrasonic and metallurgical oxide scale thickness have a correlation factor of 0.923 out of 1.00. Based on the linear least square curve fit technique, the ultrasonic and metallurgical results are related by the following equation:

$$\text{Oxide Thickness} = (0.1619 \times (\text{ToF}_2 - \text{ToF}_1)) - 1.42$$

where oxide thickness is in mils and ToF is in nanoseconds.

The ultrasonic test frequency depends upon the nominal value of the scale thickness to be measured. To resolve the interfaces, the scale thickness must be at least one wavelength of the ultrasound. The wavelength is determined by the velocity of sound in the material being inspected and the frequency of the transducer being used according to the relationship of velocity equaling the multiplication of the frequency and wavelength. Table 2 illustrates the minimum scale thickness that can be resolved at various frequencies in steel where the velocity is conservatively approximated at $2.338 \times 10^5$ in/sec.

TABLE 2

| Ultrasonic Frequency MHz | Wavelength inches |
|---|---|
| 0.5 | .4676 |
| 1.0 | .2338 |
| 2.25 | .1039 |
| 5.0 | .0476 |
| 10 | .02338 |
| 25 | .00935 |
| 50 | .00467 |
| 100 | .00234 |

Since the velocity of sound in scale is not known and will vary in scales of different compositions, the time of flight technique does not produce an absolute or exact scale thickness. However, the time of flight data is related to actual scale thickness measurement established by physical techniques such as metallurgical examination. An actual scale thickness standard is predetermined by subjecting a plurality of samples of the boiler tubes which include varying thickness of the scale to ultrasonic pulses to determine the time of flight within the scale by the techniques described herein. Thereafter, the scale on the samples is physically measured and a formula or correlation curve relating scale thickness to the time of flight of the pulses in the scale is established. This predetermined standard, i.e. curve or formula, is used in further testing thereby obviating the need for future destructive tests. Thus, a standard can be established for a particular type of scale by a correlation, by formula or by a curve of the type shown in FIG. 3.

Testing has established that frequencies on the order of 5 and 10 MHz cannot be used to measure the thickness of oxide scale although testing indicated that a highly damped 10 MHz transducer with a laboratory grade pulser/receiver and oscilloscope can detect but not measure the presence of scale on the inner surface of a boiler tube when the thickness of the scale is greater than 0.007 inches.

In operation, the ultrasonic transducer is positioned on an elongated boiler tube within a boiler. The transducer may be placed directly in contact with the outer surface of the boiler tube or closely-spaced in relation thereto by the use of an appropriate couplant. The transducer is aligned so that the centerline of the ultrasonic beam which it will produce is directed perpendicular to the inside surface of the boiler tube so that the incident beam will produce reflected beams that return to the transducer. The transducer is energized to transmit an ultrasonic pulse having a minimum frequency of 50 MHz into the boiler tube. The time of flight of the ultrasonic pulse transmitted to and reflected from the tube/scale interface of the oxide scale at the inner surface of the tube is measured. Similarly, the time of flight of the ultrasonic pulse transmitted to and reflected from the scale/fluid interface within the tube is measured. The difference between the two times of flight, i.e. the time of flight within the scale, is used to determine the thickness of the oxide scale. Most typically, this technique will be applied to areas of the boiler tubes that contain steam and which, accordingly, are more susceptible to a high temperature, relatively homogenized oxide scale formation.

The ultrasonic transducer preferably utilizes a contact technique which produces sufficient ultrasound to be transmitted into the boiler tube so that sufficient high frequency ultrasound can be reflected from the tube/scale interface and allow resolution from the reflection which will occur at the inside surface of the tube.

The invention claimed is:

1. A method for ultrasonically measuring high temperature oxide scale on the cylindrical inner surface of a fluid containing boiler tube within a boiler, which comprises the steps of:

providing a standard relating the high temperature oxide scale thickness to the time of flight of an ultrasonic pulse within the high temperature oxide scale:

positioning an ultrasonic transducer in an orientation on the outer surface of the boiler tube for directing transmission of an ultrasonic pulse into the boiler tube so that the centerline of the ultrasonic beam is perpendicular to the inner surface of the boiler tube;

energizing the transducer to transmit an ultrasonic pulse having a frequency of at least 50 MHz into the boiler tube;

measuring a first time of flight representative of the time for the ultrasonic pulse to be transmitted to and reflected from the tube/scale interface;

measuring a second time of flight representative of the time for the ultrasonic pulse to be transmitted to and reflected from the scale/fluid interface;

determining the difference between the second time of flight and the first time of flight;

comparing the difference to the standard to determine the scale thickness; and wherein the standard is prepared by first subjecting a plurality of samples of the boiler tube including scale of varying thicknesses to ultrasonic pulses to determine the time of flight within the high temperature oxide scale, physically measuring the thicknesses of the high temperature oxide scale on the respective samples, and then correlating the physical thickness measurements of the high temperature oxide scale with the time of flight of the ultrasonic pulse in the high temperature oxide scale.

2. A method for ultrasonically measuring high temperature oxide scale as claimed in claim 1 further comprising the step of placing a hand-held contact transducer manually on the outer surface of the boiler tube.

3. A method for ultrasonically measuring high temperature oxide scale as claimed in claim 1 wherein said standard is a formula relating scale thickness to the difference between the second time of flight and the first time of flight.

4. A method for ultrasonically measuring high temperature oxide scale as claimed in claim 1 wherein said standard is a correlation curve relating scale thickness to the difference between the second time of flight and the first time of flight.

* * * * *